United States Patent
Strovel et al.

(10) Patent No.: US 7,427,473 B2
(45) Date of Patent: Sep. 23, 2008

(54) CHEMO-CENTRIC SELECTION OF DISEASE-RELATED GENETIC PROFILES

(75) Inventors: Jeffrey W. Strovel, North Potomac, MD (US); David Bol, Gaithersburg, MD (US); Paul E. Young, Potomac, MD (US)

(73) Assignee: Avalon Pharmaceuticals, Inc., Germantown, MD (US)

( * ) Notice: Subject to any disclaimer, the term of this patent is extended or adjusted under 35 U.S.C. 154(b) by 0 days.

(21) Appl. No.: 10/590,256

(22) PCT Filed: Feb. 24, 2005

(86) PCT No.: PCT/US2005/005996

§ 371 (c)(1),
(2), (4) Date: Aug. 22, 2006

(87) PCT Pub. No.: WO2005/082030

PCT Pub. Date: Sep. 9, 2005

(65) Prior Publication Data

US 2007/0184447 A1      Aug. 9, 2007

Related U.S. Application Data

(60) Provisional application No. 60/547,526, filed on Feb. 25, 2004.

(51) Int. Cl.
*C12Q 1/68* (2006.01)
(52) U.S. Cl. .......................................................... 435/6
(58) Field of Classification Search ....................... None
See application file for complete search history.

(56) References Cited

OTHER PUBLICATIONS

Kihara et al, Cancer Res. 61: 6474 (2001).*
Scherf et al, Nature Genetics 24: 236 (2000).*

* cited by examiner

*Primary Examiner*—James Martinell
(74) *Attorney, Agent, or Firm*—Elliot M. Olstein; Alan J. Grant

(57) ABSTRACT

Methods for the identification of disease-related gene sets and expression nprofiles, based on common chemical modulation using a specific chemical compound are disclosed.

27 Claims, 1 Drawing Sheet

CHEMO-CENTRIC SELECTION OF DISEASE-RELATED GENETIC PROFILES

This application claims priority of U.S. Provisional Application Ser. No. 60/547,526, filed 25 Feb. 2004, the disclosure of which is hereby incorporated by reference in its entirety.

FIELD OF THE INVENTION

The present invention relates to methods of utilizing biologically active compounds for the identification and selection of gene sets having characteristic expression profiles for an identifiable disease process, including use of compound-responsive gene signatures to predict sensitivity and resistance to experimental therapeutics.

BACKGROUND OF THE INVENTION

Many different agents are known to possess biological activity, including therapeutic activity, and for many of these the molecular mechanism of action is known. Thus, such compounds may be determined to be related to each other in that they have a common mechanism of action, which mechanism may bear some relationship to the chemical properties of the compounds or to their overall molecular shape. Alternatively, such compounds may not be similar in overall molecular shape or properties but may still, for diverse reasons, operate biologically in a similar manner. In addition, such compounds, related by mechanism of action (MOA) may also show other properties in common and thus these MOA-related sets of compounds may be formed into distinct groups based on their common biological activity.

In a similar way, diverse cells may be related in terms of their susceptibility to a given chemical agent, or test compound, which may act by modifying the expression profile of a given set of genes within the genome of the cells. Thus, an expression profile may be formulated for a given gene set, the latter being some subset of the genome of the cell, and this expression profile may be modulated by the presence of a particular chemical agent. It would be advantageous to be able to take advantage of such a relationship based on common expression profiles, especially where the given gene set is related to a disease process or to the viability of the cell.

Because methods of analyzing gene expression are subject to use in large screening assays, where such methods, including rapid measurement of messenger RNA species coupled with methods of reverse transcriptase-polymerase chain reaction amplification for ease of measurement, are susceptible to high degrees of automation, such genetic methods present themselves as a ready medium for high throughput screening for agents having a selected biological activity.

Heretofore many expression profiles of diverse gene sets of different cells have been determined and most are available in public data bases. In addition, workers in the disease treatment area have attempted to determine expression profiles of cells in different diseases, such as cancer, in the hopes of finding an agent that changes the expression profile and thereby serves to alleviate the disease condition, such as by killing the cell involved (for example, a cancer cell). However, one problem with this approach is that one does not know beforehand whether a given disease is amenable to treatment with a given therapeutic agent and consequently large scale screening processes have been developed, with time and expense a major factor. Since many known therapeutic agents are already available it would be advantageous if one could ascertain the likelihood that a given cell would be susceptible to a given agent before embarking on large scale screening processes.

The present invention solves this problem by taking advantage of such methods to provide expression profiles of different cells. In so doing, the likely susceptibility of a cell to a selected therapeutic agent can be determined by finding cells with the same gene expression profile as a cell known to be susceptible to said therapeutic agent and where said agent modulates the expression profile of the given gene set.

BRIEF SUMMARY OF THE INVENTION

In one aspect, the present invention relates to a method for identifying a cell susceptible to a selected chemical agent, comprising:

(a) identifying a cell susceptible to a test compound wherein said susceptibility depends on a change in expression profile of a set of genes whose expression levels are changed in the susceptible cell due to said test compound (b) identifying a different cell from said susceptible cell wherein said different cell expresses the set of genes in the absence of treatment with test compound (a) with the expression profile of said set of genes of said susceptible cell in the absence of treatment with a test compound, wherein said expression profile identifies said different cell as being a cell susceptible to said test compound thereby identifying said different cell as a cell susceptible to said selected chemical agent.

In another aspect, the present invention relates to a method for identifying a cell susceptible to a selected chemical agent, comprising:

(a) contacting a test compound with a cell and determining inhibition of growth of said cell due to said contacting thereby identifying said cell as a susceptible cell, (b) determining a change in the expression profile of a set of genes expressed by said susceptible cell wherein said change is due to said contacting thereby identifying said set of genes as an affected gene set, (c) determining the expression profile of said affected gene set of said susceptible cell in the absence of said contacting and thereby identifying a basal expression profile for said affected gene set, (d) determining said basal expression profile for said affected gene set for a different cell from said contacted cell, wherein said basal expression profile for said affected gene set indicates a cell susceptible to said test compound thereby identifying said different cell as a cell susceptible to said selected chemical agent.

In another aspect, the present invention relates to a method for treating a disease in a mammal comprising administering to a mammal afflicted with said disease of a therapeutically effective amount of the test compound above wherein said disease is caused by a cell having the basal expression profile of the above-recited gene set. In a preferred embodiment, the mammal is a human patient and said disease is cancer.

In a separate aspect, the present invention relates to a method of identifying a cancer patient likely to respond positively to treatment with a selected anti-neoplastic agent comprising evaluating said patient's cancer for the presence of a cell equivalent to a different cell as identified by the method of the invention wherein said anti-neoplastic agent is the test compound of the invention.

In an alternative aspect, the present invention relates to a method of identifying a cancer patient unlikely to respond positively to treatment with a selected anti-neoplastic agent comprising evaluating said patient's cancer for the absence of a cell equivalent to a different cell as identified by the method of the invention wherein said anti-neoplastic agent is the test compound of the invention.

DEFINITIONS

Figure 1:
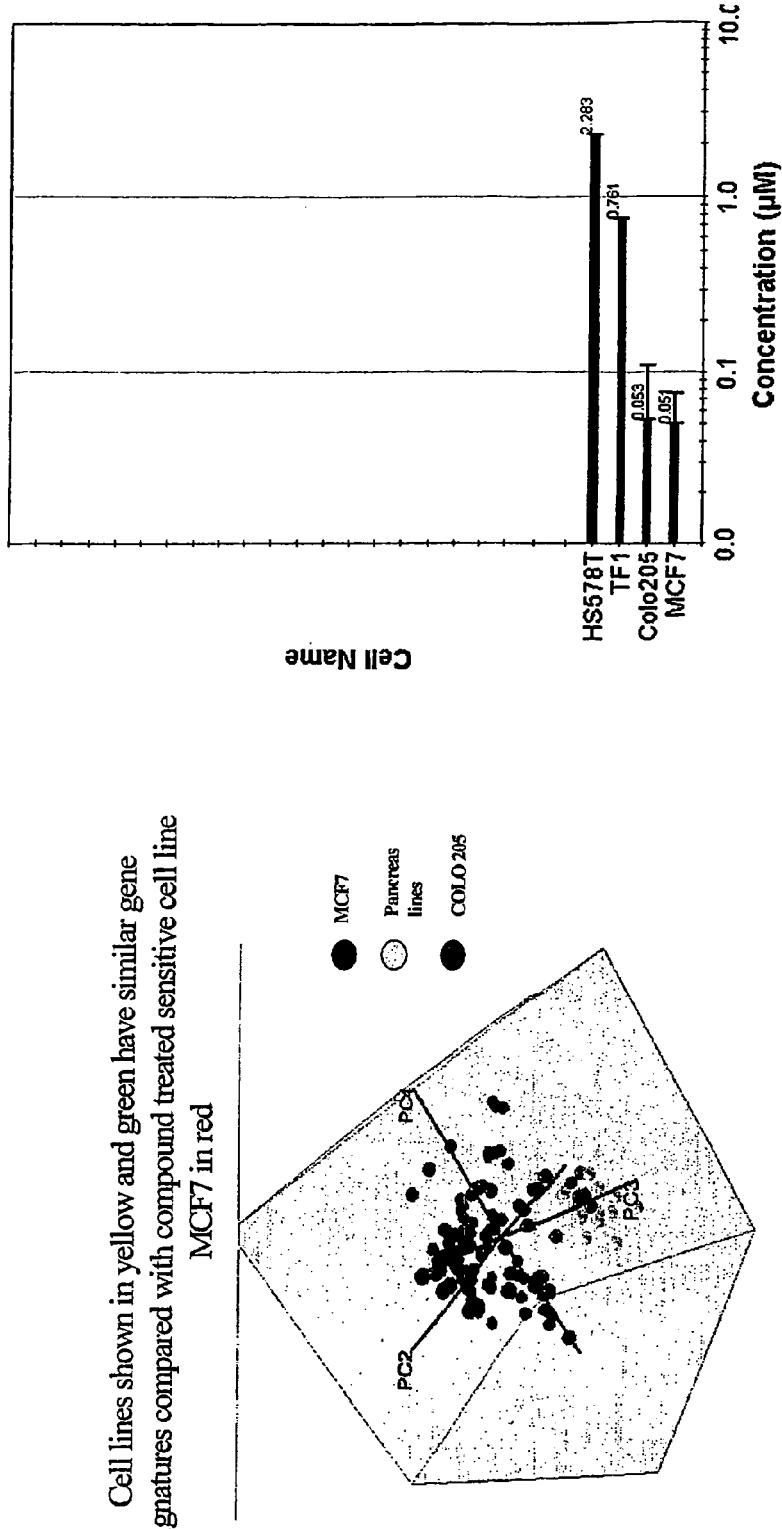
FIG. 1 shows a compound-centric approach to selection of sensitive and resistant cell lines, yielding a cell line, dubbed colo205, that is as sensitive as the original cell line (MC F-7) and 2 lines that are more than 10 fold less sensitive by growth inhibition. Thus, the present invention is useful in identifying cells as sensitive or more resistant to reference cells.

As used herein, unless expressly stated otherwise, the following terms have the indicated meaning.

In accordance with the present invention, the term "DNA segment" or "DNA sequence" refers to a DNA polymer, in the form of a separate fragment or as a component of a larger DNA construct, which has been derived from DNA isolated at least once in substantially pure form, i.e., free of contaminating endogenous materials and in a quantity or concentration enabling identification, manipulation, and recovery of the segment and its component nucleotide sequences by standard biochemical methods, for example, using a cloning vector. Such segments are provided in the form of an open reading frame uninterrupted by internal non-translated sequences, or introns, which are typically present in eukaryotic genes Sequences of non-translated DNA may be present downstream from the open reading frame, where the same do not interfere with manipulation or expression of the coding regions.

The term "coding region" refers to that portion of a gene which either naturally or normally codes for the expression product of that gene in its natural genomic environment, i.e., the region coding in vivo for the native expression product of the gene. The coding region can be from a normal, mutated or altered gene, or can even be from a DNA sequence, or gene, wholly synthesized in the laboratory using methods well known to those of skill in the art of DNA synthesis.

In accordance with the present invention, the term "nucleotide sequence" refers to a heteropolymer of deoxyribonucleotides. Generally, DNA segments encoding the proteins provided by this invention are assembled from cDNA fragments and short oligonucleotide linkers, or from a series of oligonucleotides, to provide a synthetic gene which is capable of being expressed in a recombinant transcriptional unit comprising regulatory elements derived from a microbial or viral operon.

The term "expression product" means that polypeptide or protein that is the natural translation product of the gene and any nucleic acid sequence coding equivalents resulting from genetic code degeneracy and thus coding for the same amino acid(s).

The term "promoter" means a region of DNA involved in binding of RNA polymerase to initiate transcription. The term "enhancer" refers to a region of DNA that, when present and active, has the effect of increasing expression of a different DNA sequence that is being expressed, thereby increasing the amount of expression product form ed from said different DNA sequence.

The term "open reading frame (ORF)" means a series of triplets coding for amino acids without any termination codons and is a sequence (potentially) translatable into protein.

As used herein, reference to a DNA sequence includes both single stranded and double stranded DNA. Thus, the specific sequence, unless the context indicates otherwise, refers to the single strand DNA of such sequence, the duplex of such sequence with its complement (double stranded DNA) and the complement of such sequence.

The term "percent identity" or "percent identical," when referring to a sequence, means that a sequence is compared to a claimed or described sequence after alignment of the sequence to be compared (the "Compared Sequence") with the described or claimed sequence (the "Reference Sequence"). The Percent Identity is then determined according to the following formula:

Percent Identity=$100[1-(C/R)]$ wherein C is the number of differences between the Reference Sequence and the Compared Sequence over the length of alignment between the Reference Sequence and the Compared Sequence wherein (i) each base or amino acid in the Reference Sequence that does not have a corresponding aligned base or amino acid in the Compared Sequence and (ii) each gap in the Reference Sequence and (iii) each aligned base or amino acid in the Reference Sequence that is different from an aligned base or amine acid in the Compared Sequence, constitutes a difference; and R is the number of bases or amino acids in the Reference Sequence over the length of the alignment with the Compared Sequence with any gap created in the Reference Sequence also being counted as a base or amino acid.

If an alignment exists between the Compared Sequence and the Reference Sequence for which the percent identity as calculated above is about equal to or greater than a specified minimum Percent Identity then the Compared Sequence has the specified minimum percent identity to the Reference Sequence even though alignments may exist in which the hereinabove calculated Percent Identity is less than the specified Percent Identity.

As used herein, the terms "portion," "segment," and "fragment," when used in relation to polypeptides, refer to a continuous sequence of residues, such as amino acid residues, which sequence forms a subset of a larger sequence. For example, if a polypeptide were subjected to treatment with any of the common endopeptidases, such as trypsin or chymotrypsin, the oligopeptides resulting from such treatment would represent portions, segiments or fragments of the starting polypeptide. When used in relation to a polynucleotides, such terms refer to the products produced by treatment of said polynucleotides with any of the common endonucleases, or any stretch of polynucleotides that could be synthetically synthesized.

The term "correspond" means that the gene has the indicated nucleotide sequence or that it encodes substantially the same RNA as would be encoded by the indicated sequence, the term "substantially" meaning about at least 90% identical as defined elsewhere herein and includes splice variants thereof.

The term "corresponding genes" refers to genes that encode an RNA that is at least 90% identical, preferably at least 95% identical, most preferably at least 98% identical, and especially identical, to an RNA encoded by a nucleotide sequences. Such genes will also encode the same polypeptide sequence as any of said sequences, but may include differences in such amino acid sequences where such differences are limited to conservative amino acid substitutions, such as where the same overall three dimensional structure, and thus the same antigenic character, is maintained. Thus, amino acid sequences may be within the scope of the present invention where they react with the same antibodies that react with polypeptides encoded by genes that function within the methods of the present invention.

The term "related gene set" refers to a set of genes, perhaps 5, 10 or more genes, such as those corresponding to the sequences disclosed herein, whose pattern of expression in a cell, expression is modulated by a given set of biologically active agents, especially where said agents exert said activity by a common molecular mechanism.

As used herein, the terms "gene expression profile" or "gene expression fingerprint" are interchangeable and refer to the pattern of gene expression modulation, including increase or decrease of expression, exhibited by an the members of a set of chemical agents with established biological activity when determined using a related gene set. Thus, for a set of 10 genes, possibly genes 1-6 are reduced in expression and genes 7-10 are increased in expression after contact with each of a set of agents having common biological activity. These genes represent a related gene set. The profile or fingerprint will include the relative degree of increase or decrease of expression of the genes of the set in response to the presence of a given concentration of an established biologically active agent (for example, expression of gene 1 may be reduced by half, gene 2 by ⅔, gene 3 not expressed at all, gene 7 doubled in expression, gene 10 increased 3 fold in expression, and so on in response to each of the compounds of the set and relative to the steady state levels of said genes). In the typical case, compound A is introduced into the growth medium of the cells. The result is a gene expression profile, or gene expression fingerprint, or expression fingerprint, for compound A and other compounds of the set possessing common biological activity.

As used herein, the term "test compound" refers to a chemical compound, including small organic compounds or even larger structures, such as proteins or anti-sense agents, that are used to determine the susceptibility of the growth and/or viability of a cell following contact with the test compound and where the test compound is known to modulate, or change, either by decreasing or increasing expression, the expression profile of an identifiable set of genes within the genome of the cell susceptible to said test compound.

"Basal gene expression" refers to the expression of a gene, or set of genes, when said genes, or a cell containing said genes, is not in contact with a test compound. Such expression may be measured by determining amount or rate of synthesis of RNA or protein (i.e., by transcription or translation) of by determining the level of enzyme activity of enzymes encoded by one or more of the genes of a gene set.

"Affected gene set" refers to a set of genes, being a subset of the genome of a cell, whose expression profile is altered by contacting the gene set, or a cell expressing the gene set, with a test compound where the cell is susceptible to the test compound and said susceptibility is related to, or caused by, a change in the expression profile of the gene set. When the cell is not contacted with said test compound the expression profile of the affected gene set would be deemed the basal expression profile. A gene set present in a cell different from the susceptible cell and not in contact with a test compound would be deemed an affected gene set if said gene set is Made up of genes each of which corresponds to a gene of an affected gene set of a susceptible cell in contact with a test compound.

"Susceptible cell" refers to a cell whose growth is modulated or altered, especially decreased, after contact with a test compound and where said modulation is related to, or dependent upon, a change in the expression profile of an affected gene set. Such modulation or alteration of cell growth may be manifested as a cessation of cell multiplication, a decrease in metabolic activity of the cell or even death of the cell. A 'susceptible cell' is essentially any cell that responds with gene movements upon compound treatment (i.e., contacting with a test compound). A cell is determined to be susceptible to a particular chemical agent (i.e., a test compound) by assays that measure changes in such activities as growth inhibition, apoptosis, cell invasion and migration, and xenograft efficacy studies, all of which are designed to determine if a cell line is eradicated or will be eradicated upon treatment of the cell with a test compound. In accordance with the present invention, once the cell is determined susceptible, the gene expression is used to gather all cells that are likely to be susceptible to the agent.

As used herein, any algorithm that deems a test sample to share common gene expression patterns or gene expression copy numbers with that of the original sensitive cell line defines similarity. These methods can be comprised of clustering methods such as hierarchichal, principal component analysis, K-means, or profile matching (using pearson or spearman scores, etc).

DETAILED SUMMARY OF THE INVENTION

The present invention discloses a method by which treatment-induced gene expression signatures are used to classify cancer indications, tumor models, and eventually patient populations that would be either sensitive or resistant to treatment with a class of compounds. This process could dramatically speed up drug discovery and lead optimization by directing a screening program to the most sensitive indications and tumor models for which the compounds are most suited. Presently, this is accomplished by determining the MOA or target of a compound series and then assaying tumor samples for the presence of such target in the hope that presence of the target correlates with sensitivity to the compound.

When the target of a compound is not known, however, basal gene expression levels from groups of sensitive and resistant samples would be compared to find genes or signatures associated with sensitivity to the compound series. This process is time consuming and expensive. The present invention solves this problem by offering a method wherein one does not need to know the MOA of a compound series or to compile samples proven to be sensitive or resistant to treatment. Thus, application of the methods of the present invention saves both time and money and requires only determining a treatment-induced genetic signature. The latter is then compared with basal gene expression in tumor samples to find other tumor indications, tumor models, and patient populations that will likely be amenable to treatment with the compound of interest.

The methods of the invention thus describe a compound-centric approach for the detection of cell lines and clinical samples that are sensitive to treatment with a compound class. The method comprises treating sensitive cell lines with a compound to determine a gene signature related to the action of the compound. This gene signature is screened (for example, virtually, such as by relying on data analysis software on the entire GX2000 database of cell lines and clinical samples) on other cell lines and clinical samples to find samples with a similar (note below) basal gene signature to that of the original cell line's resting signature for those genes. Cell lines and samples that contain similar gene expression patterns to the original sensitive cell line can be tested for sensitivity to the compound family (see FIG. 1).

Thus, the present invention provides a method of using the gene signature induced by compounds to find a sensitive, and thus amenable to treatment, population of cells, tumors, or patients.

The methods of the present invention find use in screening gene sets to find compounds that will exhibit a specific signature related to cancer cell sensitivity. They also find use as PD markers (i.e., a therapeutic set used to monitor chemotherapy for a particular compound class and to set the dosing requirements of compounds by monitoring the gene expression pattern in lymphocytes or other easily obtained tissue) as well as in patient population stratification into those likely to be responders versus non-responders. Use of the methods of the invention permits lead optimization programs will be faster and more efficient because the proper indications for a compound class as well as the proper tumor models for in vivo studies can be picked up much earlier in the process, especially in cases where the target of the compound is unknown.

Thus, the present invention relates to a method for identifying a cell susceptible to a selected chemical agent, comprising:

(a) identifying a cell susceptible to a test compound wherein said susceptibility depends on a change in expression profile of a set of genes whose expression levels are changed in the susceptible cell due to said test compound (b) identifying a different cell from said susceptible cell wherein said different cell expresses the set of genes in the absence of treatment with test compound of (a) with the expression profile of said set of genes of said susceptible cell in the absence of treatment with a test compound, wherein said expression profile identifies said different cell as being a cell susceptible to said test compound thereby identifying said different cell as a cell susceptible to said selected chemical agent.

In accordance with the present invention, an expression profile of an affected gene set might be determined as follows, although other means certainly present themselves to those skilled in the art. Model cellular systems using cell lines, primary cells, or tissue samples are maintained in growth medium and may be treated with compounds at a single concentration or at a range of concentrations. At specific times after treatment, cellular RNAs are isolated from the treated cells, primary cells or tissues, which RNAs are indicative of expression of the different genes. The cellular RNA is then divided and subjected to analysis that detects the presence and/or quantity of specific RNA transcripts, which transcripts may then be amplified for detection purposes using standard methodologies, such as, for example, reverse transcriptase polymerase chain reaction (RT-PCR), etc. The presence or absence, or levels, of specific RNA transcripts are determined from these measurements and a metric derived for the type and degree of response of the sample versus the steady state levels of such transcripts when the compound is not present. The relative levels of RNA transcripts following said contacting with each of a set of agents having established biological activity, including therapeutic activity, such as anti-neoplastic activity, and/or enzyme inhibitory activity and the like serves to define a related gene set and the expression profile of this set provides the fingerprint for the established biologically active agent.

The present invention also provides screening assays for identifying biologically active agents, whether the underlying chemical structures are novel or otherwise, based on the action of such agents to modulate such gene sets in a manner similar to that of an established biologically active agent.

In one embodiment of the invention, an established biologically active agent, such as an agent found to inhibit the growth or metastasis of, or kill, cancerous cells, is used to identify a set of cancer related genes by determining the genes present in a cancerous cell whose expression is modulated when said cell is contacted with an agent (i.e., a test compound), such as one having established biological activity, including therapeutic activity, such as anti-neoplastic activity, and/or enzyme inhibitory activity and the like. Thus, as a result of such contacting, genes whose expression changed versus when said contacting does not occur (i.e., the steady state levels of such gene expression), are found to show increased or decreased expression, related to the therapeutic effect of the test compound, may then be grouped as an affected gene set (in this case, a cancer-related gene set).

In a highly specific but non-limiting example, where said biological activity is anti-neoplastic activity, an established anti-neoplastic agent, compound A, is determined to modulate the expression of 10 genes found in a colon cancer cell, such as an adenocarcinoma, whereby genes these genes show a varying pattern of expression following contacting of the cell with compound A. For example, genes 1 to 7 show reduced expression, or non-expression, while genes 8 to 10 show expression, or increased expression, as a result of said contacting. This set of 10 genes thus represents a cancer related gene set as defined herein. Each of said 10 genes may be modulated to a different extent by said established anti-neoplastic agent. For example, expression of gene 1 may be reduced to a level where expression is no longer detected while gene 2 is reduced to half its expression when compound A is not present. The relative levels of expression of each of the genes in the presence and absence of compound A serves to establish an expression pattern, or expression profile. Expression in the absence of contacting with such test compound establishes a basal expression profile.

In accordance with the invention, once a basal expression profile is known for an identified affected gene set other cells and tissues, related or unrelated to a susceptible cell, can then be determined by finding a similar basal expression profile for the same gene set in other cells and tissues. One way to do this is through the use of databases, including public databases, that provide expression levels of identified genes in diverse cells and tissues from varied sources and from different species. Thus, the susceptible cell and the affected gene set may be identified using a cell from one species, such as a mouse, and then a similar gene set and basal expression profile may be determined for a cell from a different species, such as a human being.

In carrying out the methods of the invention, it is not essential to determine the identity of the test compound, susceptible cell, affected gene set and basal expression profile de novo as part of the methods of the invention. These may already be known and such information may already be available in publicly available sources. Once this information is attained, the initial steps of the claimed method are deemed to have been carried out.

In one embodiment, the present invention relates to a method for identifying a cell susceptible to a selected chemical agent, comprising:

(a) contacting a test compound with a cell and determining inhibition of growth of said cell due to said contacting thereby identifying said cell as a susceptible cell, (b) determining a change in the expression profile of a set of genes expressed by said susceptible cell wherein said change is due to said contacting thereby identifying said set of genes as an affected gene set, (c) determining the expression profile of said affected gene set of said susceptible cell in the absence of said contacting and thereby identifying a basal expression profile for said affected gene set, (d) determining said basal expression profile for said affected gene set for a different cell from said contacted cell, wherein said basal expression profile for said affected gene set indicates a cell susceptible to said test compound thereby identifying said different cell as a cell susceptible to said selected chemical agent.

In a preferred embodiment, said inhibition of growth is the death of said susceptible cell. In other such embodiments, said inhibition of growth is a cessation of multiplication of said susceptible cell or a decrease in the metabolism of such cell.

In specific embodiments of any of the methods of the invention, the different cell is a cell of the same tissue type as said susceptible cell, preferably of the same species as said susceptible cell. In addition, said susceptible cell may be a cancer cell and/or said different cell is a cancer cell. In one embodiment, the susceptible cell is a recombinant cell, including a cell genetically engineered to express an affected gene set. In another embodiment, the different cell is a non-cancer cell. In preferred embodiments, the susceptible cell is a human cell and/or the different cell is a human cell.

In other embodiments of any of the methods of the invention, identification of the susceptible cell and test compound comprise retrieving such information from a database, such as a public database. In addition, the determining in step (c) of the above-recited method may comprise retrieving the basal expression profile of the affected set, as well as identification of the affected set where the mechanism of action of the test compound is known, from a database, such as a public database. In another such embodiment, the determining in step (d) comprises retrieving said basal expression profile from a database, such as a public database. In one such embodiment, the determining of steps (c) and (d) each comprises retrieving said basal expression profile from a database, such as a public database.

In other embodiments of the above-recited method, the expression is transcription. In addition, the change in expression profile of step (b) may be determined by determining synthesis of RNA, including either amount of RNA produced, rate of production, or both. In another embodiment, the change in expression profile of step (b) is determined by determining polypeptide synthesis. In a further such embodiment, the change in expression profile of step (b) is determined by determining enzyme inhibitory activity. The identify an expression profile, such determining may be a combination of the foregoing, such as where transcription to produce RNA is determined, or known, for some genes and protein synthesis and/or activity is determined, or known, for others. In addition, it may be known for some genes of an affected gene set and determined for other genes of an affected gene set.

In another aspect, the present invention relates to a method for treating a disease in a mammal comprising administering to an mammal, preferably a human patient, afflicted with said disease of a therapeutically effective amount of the test compound, or an agent of the same class or mechanism of action of the test compound, wherein said disease is caused by a cell having the basal expression profile of an affected gene set in a cell known to be susceptible to said test compound, or compounds of the same class, such as those having similar structure or general physiological function, or mechanism of action as the test compound. In a preferred embodiment, said disease is cancer and said test compound is an anti-neoplastic agent, such as a known anti-neoplastic agent.

In an additional embodiment, the susceptible cell of (a) is a colon cell, such as a colon cancer cell. The cells utilized in the methods of the invention may also be recombinant cells engineered to express the determined genes, such as one or more genes of an affected gene set, including where the recombinant cell does not express the determined genes absent being engineered to do so, such as by genetic engineering.

In one embodiment, the test compound of step (a) is not an agent possessing known biologically activity so that the methods of the invention find use in identifying novel agents with a selected biological activity. The invention is then useful in locating other cells and tissues having a similar gene-based susceptibility to the test compound.

Thus, the present invention further relates to compounds identified as having biological activity by the methods of the invention. In preferred embodiments, such identified compounds have therapeutic activity, and/or anti-neoplastic activity, and/or enzyme inhibitory, as first determined by the methods disclosed herein but such activity is realized using cells or tissues whose susceptibility, or resistance, to the effects of the test compound were not theretofore appreciated.

The present invention also relates to a method for treating a disease comprising administering to an animal afflicted with said disease of a therapeutically effective amount of a compound identified by the methods of the invention as having therapeutic activity with a tissue different from one of known susceptibility. In a preferred embodiment, said therapeutic activity is anti-neoplastic activity.

Thus, the invention also encompasses cases where the agent, or test compound, may have been known to have a biological activity in one kind of cell but not others that can be tested using the methods herein. In addition, such known, or suspected, biological activity may have been previously determined to involve a different molecular mechanism than utilized by the methods of the present invention.

In one embodiment, the affected gene set is a cancer related gene set, identified by the modulation of all of its member genes by a given anti-neoplastic agent.

The methods of the present invention also find use in the stratification of patient populations into those likely to be responders (to a therapeutically active test compound) and those likely to be non-responders (i.e., resistant) to such agent.

In accordance therewith, the present invention relates to a method of identifying a cancer patient likely to respond positively to treatment with a selected anti-neoplastic agent comprising evaluating said patient's cancer for the presence of a cell equivalent to a different cell as identified by the method of the invention wherein said anti-neoplastic agent is the test compound of the invention.

Alternatively, the present invention relates to a method of identifying a cancer patient unlikely to respond positively to treatment with a selected anti-neoplastic agent comprising evaluating said patient's cancer for the absence of a cell equivalent to a different cell as identified by the method of the invention wherein said anti-neoplastic agent is the test compound of the invention.

Thus, the present invention permits clinicians to determine, prior to treatment with one of the different therapeutic agents currently available, the likelihood that a patient afflicted with a particular malady will respond positively to such treatment. By way of non-limiting example only, a patient afflicted with cancer may initially be considered as a candidate for any of a vast number of known anti-neoplastic agents currently approved for such use. However, as is appreciated by clinicians, not all anti-cancer drugs are equally useful against all cancers or in all patients, even those with the same type of cancer or where the same tissue or organ is cancerous. Thus, not all patients with colon cancer may respond equally well to a given anti-neoplastic agent while an agent useful against melanoma may not be useful against sarcoma or an agent useful against ovarian cancer may not be useful against colorectal cancer. In addition, valuable time may be wasted while the spectrum of anti-cancer drugs is tried in succession or where combination treatment proves ineffectual.

The present invention affords methods for determining the likely prognosis for using a selected anti-neoplastic agent prior to use. Thus, where a given agent is known to be effective against a given cancer cell, such as a specific type of cancer or cancer of a particular organ or tissue, or where the agent is determined to have such effect, and where said effect is due to a change in the expression of a selected gene, or expression profile of a selected set of genes, whether previously known or newly determined, and a basal expression profile can be identified for this cancer-related gene set (or affected gene set), it is then possible to scan databases and other types of information sources, especially where this can be done by computerized search, for other cells and tissues, especially cancerous cells and tissues, for example, cells drawn from different types of cancers, such as melanomas, carcinomas, sarcomas and the like, or for cancers of various organs, such as ovary, colon, stomach, and the like, for information on expression of the member genes of an affected gene set, especially where said expression matches the profile of the basal expression profile of an affected gene set modulated by an established anti-cancer drug, such cancers then become likely targets of the same anti-cancer drug, or class of drugs, without the need to perform extended testing beforehand or wasting of time and money in trying drugs that may or may not work.

In sum, where a selected anti-tumor agent works via change in expression profile of a given set of genes and the basal expression profile of this gene set in a susceptible cancer cell is the same as the basal expression profile in other cells, such as other cancer cells, it is deemed likely that the same drug will also operate against those tumors.

In this way, the methods of the invention provide a means of stratifying patients into groups based on whether their cancer is of a type that contains cells expressing a gene set with the same basal expression profile as that for the same, or corresponding, gene set of a cancerous cell known to be susceptible to a selected drug wherein the latter's mechanism of action comprises a change in the expression profile of said gene set. In this way, patients with cancers of different types, or cancers derived from different organs and tissues, can be assessed for positive prognosis with a given drug prior to start of any treatment regimen, thereby achieving a substantial increase in the likelihood of successful treatment.

The methods of the invention also find use in facilitating research to develop drugs useful in the treatment of diseases such as cancer.

Any compound that has an effect on cellular processes has a gene expression signature to describe those effects in a sensitive, selective way. Compounds that act via different mechanisms of action have distinct signatures at the gene expression level. Using gene transcription detection technologies, the present invention has been used to identify the genetic signature of numerous available anticancer compounds, as well as novel compounds currently in lead optimization. Using the gene signatures specific for several selected anti-cancer test compounds, the methods of the invention were successful in determining the utility of each compound, or series of compounds, in particular types of cancer, identifying sensitive models for in vitro and in vivo evaluation, and building predictors for use in the clinical development of the test compounds.

For example, in one instance the methods of the invention, employing the particular gene expression profile of a compound series in lead optimization, led away from optimization in colon cancer cells to evaluating these compounds in leukemia cell lines.

In other cases, the use of gene expression signatures for a selected program in optimization helped identify a specific set of cell lines that were sensitive to the compounds being evaluated (see the results of FIG. 1). In addition, other data suggests that the specific signature of a selected compound is the best tool to use for identifying patient populations during the clinical development of that compound. Thus, utilizing the methods of the present invention, such decisions are made early in drug discovery to avoid expensive and time consuming efforts with little value realized while also accelerating the drug discovery process and establishing a clearer path toward clinical development of such drugs.

The gene expression profile of an affected gene set may be measured or already known. For measurement, expression is commonly assayed using RNA expression as an indicator. Thus, the greater the level of RNA (messenger RNA) detected the higher the level of expression of the corresponding gene. Thus, gene expression, either absolute or relative, such as here where the expression of several different genes is being quantitatively evaluated and compared in order to establish the gene expression profile of a test compound, for example, the genes of a related gene set as disclosed herein, is determined by the relative expression of the RNAs encoded by the various gene members of the set.

RNA may be isolated from samples in a variety of ways, including lysis and denaturation with a phenolic solution containing a chaotropic agent (e.g., triazol) followed by isopropanol precipitation, ethanol wash, and resuspension in aqueous solution; or lysis and denaturation followed by isolation on solid support, such as a Qiagen resin and reconstitution in aqueous solution; or lysis and denaturation in non-phenolic, aqueous solutions followed by enzymatic conversion of RNA to DNA template copies.

Steady state RNA expression levels (i.e., basal expression) for the genes of an affected gene set may be known in the literature or may be determined by methods disclosed below. Such steady state levels of expression are easily determined by any methods that are sensitive, specific and accurate. Such methods include, but are in no way limited to, real time quantitative polymerase chain reaction (PCR), for example, using a Perkin-Elmer 7700 sequence detection system with gene specific primer probe combinations as designed using any of several commercially available software packages, such as Primer Express software., solid support based hybridization array technology using appropriate internal controls for quantitation, including filter, bead, or microchip based arrays, solid support based hybridization arrays using, for example, chemiluminescent, fluorescent, or electrochemical reaction based detection systems.

The present invention also relates to recombinant cells engineered to contain intrachromosomally or extrachromosomally one or more genes that together form a related gene set as described herein. Such recombinant cells are genetically engineered (transduced or transformed or transfected) with suitable vectors, which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the genes of the present invention. The culture conditions, such as temperature, pH and the like, are those previously used with the host cell selected for expression, and will be apparent to the ordinarily skilled artisan.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the *E. coli*. lac or tip, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in *E. coli*.

The vector containing the appropriate DNA sequence as hereinabove described, as well as an appropriate promoter or control sequence, may be employed to transform an appropriate host to permit the host to express the protein.

As representative examples of appropriate hosts, there may be mentioned: bacterial cells, such as *E. coli, Streptomyces, Salmonella typhimurium*; fungal cells, such as yeast; insect cells such as *Drosophila* S2 and *Spodoptera* Sf9; animal cells such as CHO, COS or Bowes melanoma; adenoviruses; plant cells, etc. The selection of an appropriate host is deemed to be within the scope of those skilled in the art from the teachings herein.

Promoter regions can be selected from any desired gene using CAT (chloramphenicol transferase) vectors or other vectors with selectable markers. Two appropriate vectors are pKK232-8 and pCM7. Particular named bacterial promoters include lac, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs, such as the genes forming a related gene set as defined herein. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation.

Common methods useful herein are those described in detail in Sambrook, et al., Molecular Cloning: A Laboratory Manual, Second Edition, Cold Spring Harbor, N.Y., (1989), Wu et al, *Methods in Gene Biotechnology* (CRC Press, New York, N.Y., 1997), and *Recombinant Gene Expression Protocols, in Methods in Molecular Biology*, Vol. 62, (Tuan, ed., Humana Press, Totowa, N.J., 1997), the disclosures of which are hereby incorporated by reference.

The present invention also relates to a process that comprises a method for producing a product, such as by generating test data to facilitate identification of such product, comprising identifying an agent according to one of the disclosed processes for identifying such an agent (i.e., the therapeutic agents identified according to the assay procedures disclosed herein) wherein said product is the data collected with respect to said agent as a result of said identification process, or assay, and wherein said data is sufficient to convey the chemical character and/or structure and/or properties of said agent. For example, the present invention specifically contemplates a situation whereby a user of an assay of the invention may use the assay to screen for compounds having the desired enzyme modulating activity and, having identified the compound, then conveys that information (i.e., information as to structure, dosage, etc) to another user who then utilizes the information to reproduce the agent and administer it for therapeutic or research purposes according to the invention. For example, the user of the assay (user 1) may screen a number of test compounds without knowing the structure or identity of the compounds (such as where a number of code numbers are used the first user is simply given samples labeled with said code numbers) and, after performing the screening process, using one or more assay processes of the present invention, then imparts to a second user (user 2), verbally or in writing or some equivalent fashion, sufficient information to identify the compounds having a particular modulating activity (for example, the code number with the corresponding results). This transmission of information from user 1 to user 2 is specifically contemplated by the present invention.

In accordance with the foregoing, the present invention relates to a method for producing test data with respect to the susceptibility of a cell to a selected chemical agent, comprising:

(a) identifying a cell susceptible to a test compound wherein said susceptibility depends on a change in expression profile of a set of genes whose expression levels are changed in the susceptible cell due to said test compound (b) identifying a different cell from said susceptible cell wherein said different cell expresses the set of genes in the absence of treatment with test compound with the expression profile of said set of genes of said susceptible cell in the absence of a test compound, (c) producing test data identifying said different cell as a cell susceptible to said selected chemical agent.

What is claimed is:

1. A method for identifying a cell susceptible to a test compound, comprising:
   (a) comparing a gene expression profile of a set of genes of a test cell, said comparing being made prior to treatment of the cell with the test compound, with
   (b) an expression profile of said set of genes of a different cell known to be susceptible to treatment with said test compound, said gene expression profile of said susceptible cell being determined prior to treatment with the test compound, said set of genes being a set of genes whose gene expression profile changes in said susceptible cell in response to treatment with said test compound,
   wherein a similarity in gene expression profile for the test cell and the susceptible cell prior to treatment with said test compound identifies the test cell as susceptible to treatment with said test compound.

2. The method of claim 1 wherein said susceptibility is manifested by an inhibition of growth of said susceptible cell.

3. The method of claim 2 wherein said inhibition of growth is the death of said susceptible cell.

4. The method of claim 2 wherein said inhibition of growth is a cessation of multiplication of said susceptible cell.

5. The method of claim 1 wherein said different cell is a cell of the same tissue type as said susceptible cell.

6. The method of claim 1 wherein said different cell is a cell of the same species as said susceptible cell.

7. The method of claim 1 wherein said susceptible cell is a cancer cell.

8. The method of claim 1 wherein said different cell is a cancer cell.

9. The method of claim 1 wherein said different cell is a non-cancer cell.

10. The method of claim 1 wherein said susceptible cell is a human cell.

11. The method of claim 1 wherein said different cell is a human cell.

12. A method for treating a disease in a mammal comprising administering to a mammal afflicted with said disease a therapeutically effective amount of the test compound of claim 1 wherein said disease is caused by a cell having the expression profile of step (b) of claim 1.

13. The method of claim 12 wherein said mammal is a human being.

14. The method of claim 12 wherein said disease is cancer.

15. A method of identifying a cancer patient likely to respond positively to treatment with a selected anti-neoplastic agent comprising evaluating said patient's cancer for the presence of a cell equivalent to a different cell as identified by the method of claim 1 wherein said anti-neoplastic agent is the test compound of claim 1.

16. A method of identifying a cancer patient unlikely to respond positively to treatment with a selected anti-neoplastic agent comprising evaluating said patient's cancer for the absence of a cell equivalent to a different cell as identified by the method of claim 1 wherein said anti-neoplastic agent is the test compound of claim 1.

17. A method for identifying a cell in need of treatment with a selected chemical agent, comprising:
  (a) contacting a test compound with a cell and determining inhibition of growth of said cell due to said contacting thereby identifying said cell as a susceptible cell,
  (b) determining a change in the expression profile of a set of genes expressed by said susceptible cell wherein said change is due to said contacting thereby identifying said set of genes as an affected gene set,
  (c) determining the expression profile of said affected gene set of said susceptible cell in the absence of said contacting and thereby identifying a basal expression profile for said affected gene set,
  (d) determining said basal expression profile for said affected gene set for a different cell from said contacted cell,
  wherein said basal expression profile for said affected gene set indicates a cell susceptible to said test compound
  thereby identifying said different cell as a cell susceptible to said selected chemical agent.

18. The method of claim 17 wherein said expression is transcription.

19. The method of claim 17 wherein said change in expression profile of (b) is determined by determining synthesis of RNA.

20. The method of claim 17 wherein said change in expression profile of (b) is determined by determining polypeptide synthesis.

21. The method of claim 17 wherein said change in expression profile of (b) is determined by determining enzyme activity.

22. The method of claim 17 wherein said determining in step (c) comprises retrieving said basal expression profile from a database.

23. The method of claim 17 wherein said determining in step (d) comprises retrieving said basal expression profile from a database.

24. The method of claim 17 wherein said determining of step (c) and (d) each comprises retrieving said basal expression profile from a database.

25. A method for producing test data with respect to the susceptibility of a cell to a selected chemical agent, comprising:
  (a) identifying a cell susceptible to a test compound wherein said susceptibility depends on a change in expression profile of a set of genes whose expression levels are changed in the susceptible cell due to said test compound
  (b) identifying a different cell from said susceptible cell wherein said different cell expresses the set of genes in the absence of treatment with test compound with the expression profile of said set of genes of said susceptible cell in the absence of a test compound,
  (c) producing test data identifying said different cell as a cell susceptible to said selected chemical agent.

26. The method of claim 25 wherein said different cell is a human cell.

27. The method of claim 25 wherein said susceptible cell is a cancer cell.

* * * * *

UNITED STATES PATENT AND TRADEMARK OFFICE
CERTIFICATE OF CORRECTION

| | | |
|---|---|---|
| PATENT NO. | : 7,427,473 B2 | |
| APPLICATION NO. | : 10/590256 | |
| DATED | : September 23, 2008 | |
| INVENTOR(S) | : Jeffrey W. Strovel et al. | |

It is certified that error appears in the above-identified patent and that said Letters Patent is hereby corrected as shown below:

<u>Title Page, item [57]</u>

In the Abstract, delete "expression nprofiles" and insert therefor --expression profiles--

At column 4, line 21, delete "amine" and insert therefor --amino--

At column 5, line 43, delete "of"

At column 5, line 56, delete "Made" and insert therefor --made--

At column 12, line 47, delete "., " and insert therefor --,--

At column 13, line 11, delete "tip" and insert therefor --trp--

Signed and Sealed this

Ninth Day of December, 2008

JON W. DUDAS
*Director of the United States Patent and Trademark Office*